United States Patent [19]

Nakajima et al.

[11] 4,337,355
[45] Jun. 29, 1982

[54] PROCESS FOR PREPARING 4-HYDROXYPHENYLACETIC ACID

[75] Inventors: Kazuhisa Nakajima, Mino; Kazuaki Gohgi, Nishinomiya; Toshio Yamamoto, Suita, all of Japan

[73] Assignee: Nippon Gohsei Kagaku Kogyo Kabushiki Kaisha, Osaka, Japan

[21] Appl. No.: 161,592

[22] Filed: Jun. 20, 1980

[51] Int. Cl.³ ............................................. C07C 65/01
[52] U.S. Cl. ..................................... 562/478; 562/470
[58] Field of Search ................................ 562/478, 470

[56] References Cited

U.S. PATENT DOCUMENTS 4,198,526 4/1980 Edwards ............................ 562/475

FOREIGN PATENT DOCUMENTS 3825 2/1979 European Pat. Off. ............ 562/478

Primary Examiner—Paul J. Killos
Attorney, Agent, or Firm—Armstrong, Nikaido, Marmelstein & Kubovcik

[57] ABSTRACT

A process for preparing 4-hydroxyphenylacetic acid by reducing 4-hydroxymandelic acid in a reaction medium of a lower aliphatic carboxylic acid or a water-containing lower aliphatic carboxylic acid. When the crystalline 4-hydroxymandelic acid is employed as the staring material, 4-hydroxyphenylacetic acid of high quality is obtained in high yields.

9 Claims, No Drawings

PROCESS FOR PREPARING 4-HYDROXYPHENYLACETIC ACID

BACKGROUND OF THE INVENTION

The present invention relates to a process for preparing 4-hydroxyphenylacetic acid.

4-Hydroxyphenylacetic acid is useful as an intermediate of pharmaceuticals and agricultural chemicals.

As an industrially advantageous process for the preparation of 4-hydroxyphenylacetic acid, there is proposed a process by catalytic reduction of 4-hydroxymandelic acid, and one of the most preferable embodiment of the process is the catalytic reduction of 4-hydroxymandelic acid, especially the sodium salt thereof with palladium catalyst in water medium in the presence of a large amount of hydrochloric acid. However, such a process involves problems that (1) the yield of 4-hydroxyphenylacetic acid is at most 85% by mole to 4-hydroxymandelic acid, and that (2) because of the use of a large amount of hydrochloric acid, the desired product is contaminated with a large amount of a neutralized salt and the purification is troublesome, and an apparatus is in danger of corrosion. For these reasons, further improvements are desired in the operation and the quality of the product in the industrial production.

Accordingly, it is an object of the present invention to provide an improved process for preparing 4-hydroxyphenylacetic acid.

A further object of the invention is to provide a process for preparing 4-hydroxyphenylacetic acid of high quality in high yields.

These and other objects of the invention will become apparent from the description hereinafter.

SUMMARY OF THE INVENTION

In accordance with the present invention, there is provided a process for preparing 4-hydroxyphenylacetic acid which comprises reducing 4-hydroxymandelic acid in a reaction medium of a lower aliphatic carboxylic acid or a water-containing lower aliphatic carboxylic acid, and recovering the resulting 4-hydroxyphenylacetic acid.

There is also provided a process for preparing 4-hydroxyphenylacetic acid which comprises reacting glyoxylic acid with phenol in the presence of an alkali at a temperature of 40° to 70° C., reducing the obtained 4-hydroxymandelic acid, and recovering the resulting 4-hydroxyphenylacetic acid.

DETAILED DESCRIPTION

In the present invention, the reduction of 4-hydroxymandelic acid is carried out in a reaction medium of a lower aliphatic carboxylic acid or an aqueous solution of a lower aliphatic carboxylic acid. It is advantageous to use 4-hydroxymandelic acid of high quality as the starting material, because impurities in 4-hydroxymandelic acid disturb the reduction. When crystalline 4-hydroxymandelic acid is employed, the reduction proceeds very smoothly and 4-hydroxyphenylacetic acid of high quality is produced in high yields, e.g. in yields of 90 to 95% by mole based on the 4-hydroxymandelic acid.

The present inventors have investigated on a process of the synthesis of crystalline 4-hydroxymandelic acid, and found that when phenol and glyoxylic acid are reacted in the presence of an alkali at a temperature of 40° to 70° C., preferably 40° to 65° C., the resulting reaction mixture is extracted with a solvent and the solvent is distilled away from the extract, 4-hydroxymandelic acid can be readily obtained in the form of crystal in a short period of time in high yields.

The preferable embodiment of the process of the present invention consists of (1) a step for preparing 4-hydroxymandelic acid from phenol and glyoxylic acid and (2) a step for preparing 4-hydroxyphenylacetic acid by the reduction of the 4-hydroxymandelic acid in a definite condition, and these steps are explained below:

The preparation of 4-hydroxymandelic acid according to the present invention is characterized by (1) conducting the reaction of phenol and glyoxylic acid at a relatively high temperature region such as a temperature of 40° to 70° C., preferably 40° to 65° C. and (2) subjecting the obtained reaction mixture to extraction with a solvent and then distilling away the solvent from the extract to give crystals. Reactions of glyoxylic acid at a high temperature has hitherto been considered to be undesirable, because glyoxylic acid would convert into oxalic acid and glycolic acid by Cannizzaro reaction, and such reactions have been generally conducted at a relatively low temperature region such as room temperature. In the present invention, 4-hydroxymandelic acid is obtained unexpectedly in a short reaction time in high yields by the reaction of a high temperature contrary to the usual practice. The reaction temperature of 40° to 70° C. is an important factor in the reaction of phenol and glyoxylic acid. When the reaction temperature is raised too much, i.e. to more than 70° C., by-product, 2-hydroxymandelic acid is remarkable and the desired product is contaminated therewith to result in lowering of its quality. In order to avoid the by-production, the amount of an aqueous medium must be increased. This is also not practical in points of the extraction efficiency of the desired product from the reaction mixture and the apparatus efficiency.

Commercially available glyoxylic acid is in the form of an aqueous solution in concentrations of about 20 to about 50% by weight, but there may also be employed glyoxylic acid in various forms such as an aqueous solution diluted or concentrated and a solid glyoxylic acid hydrate.

The reaction of phenol and glyoxylic acid is usually carried out in an aqueous medium in the presence of an alkali such as sodium hydroxide, potassium hydroxide, sodium carbonate or potassium carbonate. Sodium and potassium hydroxides are particularly preferred as the alkali. Water is the most practical as the medium, but a mixture of water and an organic solvent miscible with water may also be employed.

The ratio of glyoxylic acid, phenol and an alkali is selected from glyoxylic acid:phenol:alkali = 1:0.8 to 10:1 to 5, preferably 1:1.2 to 3.5:1.2 to 4. The aqueous medium is employed suitably in an amount of not more than 80 times the number of moles of glyoxylic acid. The water in an aqueous solution of glyoxylic acid and water in an aqueous solution of an alkali are also estimated as the amount of the aqueous medium. The use of the aqueous medium in an amount of more than the above is not practical in points of the extraction efficiency and apparatus efficiency.

Admixing of glyoxylic acid, phenol and an alkali in an aqueous medium and heating of the mixture are sufficient for conducting the reaction. Any means may be adopted for charging these materials, and there is usually adopted a manner in which phenol is first dispersed into a medium, and after adding an aqueous solution of an alkali to the medium, a prescribed amount of glyoxylic acid is added in the form of an aqueous solution thereof or an aqueous solution of its alkali metal salt.

The reaction temperature is one of the important factors in the present step as mentioned before, and it is necessary to adjust the temperature exactly within the range of 40° to 70° C., preferably 40° to 65° C. By carrying out the reaction of phenol and glyoxylic acid at such a high temperature, 4-hydroxymandelic acid can be obtained in a very short time in high yields. When the reaction temperature is lower than 40° C., the reaction rate is very slow. Therefore, in case of obtaining the desired product in a practical yield, the reaction takes several days and is impractical in industrial production. On the other hand, when the reaction temperature is higher than 70° C., the quality of the obtained 4-hydroxymandelic acid is remarkably decreased. The reaction time varies to some extent depending on the reaction temperature. In general, the reaction at a temperature of 40° to 65° C. is sufficiently completed in about 3 hours.

In order to prevent the coloration of the obtained 4-hydroxymandelic acid crystal, it is desirable to carry out the reaction in an atmosphere of an inert gas such as nitrogen or argon.

After the completion of the reaction, the reaction mixture is acidified, and the unreacted phenol is removed from the reaction mixture by extraction with a suitable organic solvent such as benzene, toluene or chloroform. The secondary important factor in this step for preparing 4-hydroxymandelic acid is to extract the obtained aqueous phase with a solvent to recover the crystal of 4-hydroxymandelic acid from the aqueous phase. The crystal cannot be substantially obtained by a separation method other than extraction, e.g. by a cooling method in which the obtained aqueous phase is cooled to less than 5° C. Also, in case of a concentration method, decomposition of the desired product may take place, and in case of a salting-out method, the desired product is contaminated with a neutralization salt.

4-Hydroxymandelic acid is thus obtained in the form of an alkali metal salt, and it should be changed to the free acid by acidifying the aqueous phase. An alkali metal salt of 4-hydroxymandelic acid cannot be separated from the aqueous phase by the solvent extraction. In order to conduct efficiently the extraction operation, the aqueous phase may be concentrated previously. In that case, the concentration is conducted at pH 2 to 8.5, preferably pH 3 to 8, and at a temperature of at most 80° C., preferably at most 60° C., so that the stability of 4-hydroxymandelic acid is not impaired. It is sufficient to concentrate to 10% by weight in the concentration of 4-hydroxymandelic acid. As the solvent for extraction, there are employed organic solvents substantially immiscible with water, e.g. a lower alkyl ester of acetic acid such as methyl acetate, ethyl acetate or butyl acetate, an ether such as diethyl ether, and an aliphatic ketone such as methyl isobutyl ketone. A lower alkyl ester of acetic acid such as ethyl acetate and an aliphatic ketone such as methyl isobutyl ketone are preferred. A solvent such as benzene or chloroform is poor in extraction effect and is impractical. 4-Hydroxymandelic acid is separated from the aqueous phase by extraction with the solvent, and the solvent is removed from the extract to precipitate 4-hydroxymandelic acid as the crystal. The obtained crystal of 4-hydroxymandelic acid may be further purified by a suitable means such as treatment with active carbon or recrystallization.

The crystal of 4-hydroxymandelic acid so obtained is white or light yellow, and the purity is very high. The melting point is about 100°-105° C. The yield of the crystal to glyoxylic acid is at least 70% by mole and, therefore, the step for preparing 4-hydroxymandelic acid is industrially useful.

The step for preparing 4-hydroxyphenylacetic acid by the reduction of 4-hydroxymandelic acid is then explained below.

The reduction may be carried out in any known manners such as catalytic reduction and reduction with a chemical reagent. Catalylic reduction is industrially advantageous.

It is essential to conduct the catalytic reduction in a reaction medium of a lower aliphatic carboxylic acid such as acetic acid, propionic acid or butyric acid, or a water-containing lower aliphatic carboxylic acid. Acetic acid is particularly preferred as the aliphatic carboxylic acid. When a reaction medium other than the carboxylic acid, e.g. water alone, is employed, a large amount of a mineral acid is required and the obtained 4-hydroxyphenylacetic acid is colored to lower its quality. Addition of water to the carboxylic acid greatly prevents the 4-hydroxymandelic acid from changing to a viscous oily material of high molecular weight and, therefore, it is possible to increase the yield and quality of 4-hydroxyphenylacetic acid. The water content of the reaction medium is selected from 5 to 50% by weight, preferably 10 to 30% by weight. The use of water in an amount of less than 5% by weight is not effective for increasing the reduction rate and the yield, and on the other hand, the use of water more than 50% by weight makes the reduction rate and the yield of 4-hydroxyphenylacetic acid remarkably decrease. The presence of a proper amount of water is very advantageous for the present invention. The amount of the aliphatic carboxylic acid or the water-containing aliphatic carboxylic acid is at least 3 times the weight of 4-hydroxymandelic acid, and is employed preferably in an amount of 4 to 12 times, more preferably 6 to 10 times the weight of 4-hydroxymandelic acid.

In the catalytic reduction, there may be employed a palladium, nickel or platinum catalyst. These catalysts may be supported on a suitable carrier such as active carbon, aluminum or silica.

The reaction may be carried out under atmospheric pressure or under a pressure, and it is desirable to carry out the reaction under a pressure of several kilograms per square centimeter from viewpoint of practical reaction rate. The reaction temperature is selected from 50° to 120° C., preferably 70° to 100° C. Addition of a mineral acid such as sulfuric acid or hydrochloric acid is desired for increasing the reaction rate and yield. Although the amount of the acid to be added varies depending on the kind of the acid, it is particularly desirable to employ the acid in an amount of 0.05 to 1.0 mole, preferably 0.1 to 0.5 mole, per mole of 4-hydroxymandelic acid. The use of sulfuric acid is the most preferable among the mineral acids. Sulfuric acid produces a specific effect in this step for preparing 4-hydroxyphenylacetic acid, and it is necessary to control exactly its amount. The use of sulfuric acid in an amount within a very narrow range, i.e. in an amount of 0.1 to 0.5 mole per mole of 4-hydroxymandelic acid, produces a good result that 4-hydroxyphenylacetic acid is obtained in high yields. Such a phenomenon is peculiar to the catalytic reduction of 4-hydroxymandelic acid. For instance, in case of the reduction of 3-chloro-4-hydroxymandelic acid, the amount of sulfuric acid used is not so critical as in the present invention. It is considered that sulfuric acid is complicatedly, organically connected with the kind of a nuclear substituent in the mandelic acid, the kind of a solvent and the like.

As mentioned above, the factors affecting the yield of 4-hydroxyphenylacetic acid are (1) a lower aliphatic carboxylic acid solvent, (2) water content in the solvent, (3) kind of a mineral acid and its amount, and (4) reaction temperature. The most preferable embodiment is the catalytic reduction with a palladium catalyst characterized by (1) employing the water-containing acetic acid as a reaction medium in an amount of 4 to 12 times the weight of 4-hydroxymandelic acid, (2) containing 10 to 30% by weight of water in the reaction medium, (3) using sulfuric acid in an amount of 0.1 to 0.5 mole per mole of 4-hydroxymandelic acid and (4) maintaining the reaction temperature within the range of 70° to 100° C. It is desirable to avoid the use of water alone as the reaction medium and the use of hydrochloric acid as the mineral acid from viewpoint of the yield of the desired product and of the coloration of the product and corrosion of apparatus resulting from the use of a large amount of hydrochloric acid.

After the completion of the reduction, the catalyst is removed in a usual manner, and 4-hydroxyphenylacetic acid is obtained in the form of crystal by neutralizing a mineral acid and distilling away the solvent from the reaction mixture, or by adding water to the reaction mixture and extracting with a solvent and removing the solvent from the extract. The crystal may be further purified as occasion demands.

According to the present invention, 4-hydroxyphenylacetic acid can be obtained in a yield of at least 60% by mole to glyoxylic acid, and in a yield of at least 90% by mole to 4-hydroxymandelic acid.

The present invention is more particularly described and explained by means of the following Examples, in which all % are by weight unless otherwise noted.

EXAMPLE 1

After replacing the air with nitrogen gas, a one liter three neck flask equipped with a stirrer and a thermometer was charged with 75.2 g. (0.8 mole) of phenol and an aqueous solution of 75.7 g. of potassium hydroxide dissolved in 600 ml. of water. To the flask was then added 74.1 g. of a 50% aqueous solution of glyoxylic acid (0.5 mole). The reaction was carried out at 55° C. for 2.0 hours with stirring in a nitrogen stream. After the completion of the reaction, the reaction mixture was cooled to room temperature and was acidified with 120 g. of a conc. hydrochloric acid, and then extracted with four 200 ml. portions of benzene to remove the unreacted phenol.

The obtained aqueous layer was then extracted with 250 ml. of ethyl acetate. This extraction procedure was repeated 5 times. Ethyl acetate was distilled away from the resulting extract to give 68.5 g. of light yellow crystal of 4-hydroxymandelic acid monohydrate. The yield to glyoxylic acid was 74% by mole, and the melting point was 100°–105° C.

The infrared spectrum and nuclear magnetic resonance spectrum of the crystal agreed with those of authentic 4-hydroxymandelic acid.

In a mixture of 400 g. of acetic acid containing 18% of water and 5.5 g. (0.053 mole) of conc. sulfuric acid was dissolved 66.7 g. (0.269 mole) of the above 4-hydroxymandelic acid monohydrate. After adding 2.5 g. of a 5% palladium/carbon catalyst to the solution, the catalytic reduction was carried out at a temperature of 85° to 90° C. for 2.0 hours under a pressure of 4 kg./cm.$^2$ G of hydrogen with stirring. After the completion of the reaction, the reaction mixture was cooled and the catalyst was removed by filtration. The filtrate was neutralized with an equivalent amount of sodium hydroxide to the charged sulfuric acid, and the solvent was distilled away to give 69.3 g. of crystal of 4-hydroxyphenylacetic acid. The yield to 4-hydroxymandelic acid monohydrate was 95% by mole. The infrared spectrum and nuclear magnetic resonance spectrum of the recrystallized product agreed with those of the authentic 4-hydroxyphenylacetic acid. The product was white crystal and its quality was very good. The melting point was 151°–153° C.

EXAMPLE 2

Reaction of phenol and glyoxylic acid was carried out in the same manner as in Example 1. The resulting reaction mixture was adjusted to pH 6.0 with 61 g. of conc. hydrochloric acid, and was then extracted with three 100 ml. portions of ethyl acetate to remove the unreacted phenol.

After making the obtained aqueous layer strong-acidic by adding 65 g. of conc. hydrochloric acid, the extraction of the aqueous layer with ethyl acetate was carried out in the same manner as in Example 1 to give 67.9 g. of light yellow crystal of 4-hydroxymandelic acid monohydrate. The yield to glyoxylic acid was 73% by mole.

In a mixture of 390 g. of acetic acid containing 15% of water and 6.5 g. (0.063 mole) of conc. hydrochloric acid was dissolved in 66.7 g. (0.269 mole) of 4-hydroxymandelic acid monohydrate. After adding 3.2 g. of a 5% palladium/carbon catalyst to the solution, the catalytic reduction was carried out at a temperature of 86° to 90° C. for 1.25 hours under a pressure of 4 kg./cm.$^2$ G of hydrogen with stirring. After the completion of the reaction, the reaction mixture was treated in the same manner as in Example 1 to give 51.5 g. of violet 4-hydroxyphenylacetic acid. The yield to 4-hydroxymandelic acid monohydrate was 89.8% by mole.

EXAMPLES 3 TO 5 AND COMPARATIVE EXAMPLES 1 AND 2

The procedures of Example 1 were repeated except that upon the preparation of 4-hydroxymandelic acid monohydrate, potassium hydroxide was employed in an amount of 72.8 g. and the reaction of phenol and glyoxylic acid was conducted at a temperature shown in the following Table.

The results are shown in the Table, in which the yields are based on glyoxylic acid.

|  | Reaction temp. (°C.) | Reaction time (hour) | Yield (mole %) | |
|---|---|---|---|---|
|  |  |  | 4-Hydroxy-mandelic acid mono-hydrate | 4-Hydroxy-phenylacetic acid |
| Ex. 3 | 50 | 3 | 73 | 68 |
| Ex. 4 | 60 | 1.5 | 72 | 69 |
| Ex. 5 | 65 | 1.2 | 70 | 67 |
| Com. Ex. 1 | 0 | 160 | 66 | 63 |
| Com. | | | | |

-continued

| | Reaction temp. (°C.) | Reaction time (hour) | Yield (mole %) | |
| --- | --- | --- | --- | --- |
| | | | 4-Hydroxy-mandelic acid mono-hydrate | 4-Hydroxy-phenylacetic acid |
| Ex. 2 | 25 | 24 | 69 | 66 |

As is clear from the results of Comparative Examples, the reaction of phenol and glyoxylic acid at a low temperature requires a long reaction time of more than one day, and is not industrially practical.

EXAMPLES 6 TO 8

The procedures of Example 1 were repeated except that in the preparation of 4-hydroxymandelic acid monohydrate, the aqueous layer was extracted with methyl isobutyl ketone (Example 6), diethyl ether (Example 7) or n-butyl acetate (Example 8). The yields of 4-hydroxymandelic acid monohydrate were 73% by mole (Example 6), 42% by mole (Example 7) and 37% by mole (Example 8), respectively. Also, in each Example, the yield of 4-hydroxyphenylacetic acid to 4-hydroxymandelic acid was 94% by mole.

When benzene and chloroform were employed as the extracting solvent, a trace amount of 4-hydroxymandelic acid was merely obtained.

COMPARATIVE EXAMPLE 3

In a mixture of 480 g. of water and 33.4 g. (0.324 mole) of conc. sulfuric acid was dissolved 50.0 g. (0.269 mole) of 4-hydroxymandelic acid monohydrate, and thereto was added 3.7 g. of a 5% palladium/carbon catalyst. The catalytic reduction was carried out at a temperature of 90° to 93° C. for 4 hours under a pressure of 4 kg./cm.$^2$ G of hydrogen with stirring.

After the completion of the reaction, the reaction mixture was cooled and the catalyst was filtered. The filtrate was neutralized with an alkali, and the solvent was distilled away to dryness to give 135.5 g. of a product. The product was a mixture of 13.4% of 4-hydroxyphenylacetic acid, 9.7% of the starting material and 76.9% of their salts, and the yield of 4-hydroxyphenylacetic acid was low.

EXAMPLES 9 TO 11

The catalytic reduction was carried out in the same manner as in Example 1 except that conc. sulfuric acid was employed in an amount of 0.30 mole (Example 9), 0.05 mole (Example 10) or 0.60 mole (Example 11), per mole of 4-hydroxymandelic acid. The yields of 4-hydroxyphenylacetic acid were 94% by mole (Example 9), 75% by mole (Example 10) and 63% by mole (Example 11).

EXAMPLES 12 TO 14

The catalytic reduction was carried out in the same manner as in Example 1 except that acetic acid containing 16% of water (Example 12), 8% of water (Example 13) or 32% of water (Example 14) was employed. The yields of 4-hydroxyphenylacetic acid were 94% by mole (Example 12), 70% by mole (Example 13) and 68% by mole (Example 14).

EXAMPLES 15 AND 16

The catalytic reduction was carried out in the same manner as in Example 1 except that the water-containing acetic acid was employed in an amount of 3 times (Example 15) or 8.8 times (Example 16) the weight of 4-hydroxymandelic acid. The yields of 4-hydroxyphenylacetic acid were 78% by mole (Example 15) and 95% by mole (Example 16).

What we claim is:

1. A process for preparing 4-hydroxyphenylacetic acid which comprises reducing, in the presence of a catalyst, 4-hydroxymandelic acid in a reaction medium consisting essentially of a water-containing lower aliphatic carboxylic acid containing 5 to 50% by weight of water, and recovering the resulting 4-hydroxyphenylacetic acid.

2. The process of claim 1, wherein said lower aliphatic carboxylic acid is acetic acid.

3. The process of claim 1 or 2, wherein said reaction medium is employed in an amount of at least 3 times the weight of the 4-hydroxymandelic acid.

4. The process of claim 1, wherein said catalytic reduction is carried out in the presence of sulfuric acid.

5. The process of claim 4, wherein said sulfuric acid is present in an amount of 0.05 to 1 mole per mole of 4-hydroxymandelic acid.

6. The process of claim 1, wherein said catalytic reduction is carried out at a temperature of 50° to 120° C.

7. The process of claim 1, wherein said 4-hydroxymandelic acid is a crystalline 4-hydroxymandelic acid obtained by reacting phenol and glyoxylic acid in an aqueous medium at a temperature of 40° to 70° C., extracting the resulting reaction mixture with an organic solvent substantially immiscible with water and removing the solvent from the resulting extract.

8. The process of claim 7, wherein the reaction of phenol and glyoxylic acid is carried out at a temperature of 40° to 65° C.

9. The process of claim 7, wherein said organic solvent is a member selected from the group consisting of lower alkyl esters of acetic acid and aliphatic ketones.

* * * * *